US005865849A

United States Patent [19]
Stone

[11] Patent Number: 5,865,849
[45] Date of Patent: Feb. 2, 1999

[54] MENISCAL HETEROGRAFTS

[75] Inventor: Kevin R. Stone, Mill Valley, Calif.

[73] Assignee: Crosscart, Inc., San Francisco, Calif.

[21] Appl. No.: 483,256

[22] Filed: Jun. 7, 1995

[51] Int. Cl.⁶ .................................................. A61F 2/30
[52] U.S. Cl. ........................ 623/18; 623/11; 623/66
[58] Field of Search ............................. 623/1, 2, 11, 12, 623/66, 13; 530/356, 350, 388.22, 389.1; 435/1.2

[56] References Cited

U.S. PATENT DOCUMENTS

| | | |
|---|---|---|
| 4,034,418 | 7/1977 | Jackson et al. . |
| 4,344,193 | 8/1982 | Kenny . |
| 4,400,833 | 8/1983 | Kurland . |
| 4,502,161 | 3/1985 | Wall . |
| 4,597,266 | 7/1986 | Entrekin ........................................ 62/46 |
| 4,609,627 | 9/1986 | Goldstein . |
| 4,627,853 | 12/1986 | Campbell et al. . |
| 4,642,120 | 2/1987 | Nevo et al. . |
| 4,678,470 | 7/1987 | Nashef et al. . |
| 4,755,593 | 7/1988 | Lauren ...................................... 530/356 |
| 4,776,853 | 10/1988 | Klement et al. . |
| 4,801,299 | 1/1989 | Brendel et al. . |
| 4,846,835 | 7/1989 | Grande . |
| 4,880,429 | 11/1989 | Stone . |
| 4,932,973 | 6/1990 | Gendler ...................................... 623/16 |
| 5,007,934 | 4/1991 | Stone ......................................... 623/20 |
| 5,067,962 | 11/1991 | Campbell et al. ......................... 623/13 |
| 5,071,741 | 12/1991 | Brockbank ................................ 435/1 |
| 5,078,744 | 1/1992 | Chvapil . |
| 5,092,894 | 3/1992 | Kenny ...................................... 623/18 |
| 5,116,374 | 5/1992 | Stone . |
| 5,131,850 | 7/1992 | Brockbank ............................... 435/1 |
| 5,158,574 | 10/1992 | Stone . |
| 5,160,313 | 11/1992 | Carpenter et al. ......................... 600/36 |
| 5,171,322 | 12/1992 | Kenny ...................................... 623/18 |
| 5,171,660 | 12/1992 | Carpenter et al. ......................... 435/1 |
| 5,306,304 | 4/1994 | Gendler ..................................... 623/16 |
| 5,306,311 | 4/1994 | Stone et al. . |
| 5,358,525 | 10/1994 | Fox et al. .................................. 623/18 |
| 5,507,810 | 4/1996 | Prewett et al. . |
| 5,613,982 | 3/1997 | Goldstein ................................. 623/11 |

FOREIGN PATENT DOCUMENTS

| | | |
|---|---|---|
| WO 84/03036 | 8/1984 | WIPO . |
| WO 95/26740 | 10/1995 | WIPO . |
| WO 95/28412 | 10/1995 | WIPO . |
| WO 95/33828 | 12/1995 | WIPO . |

OTHER PUBLICATIONS

Stone et al., *Arthroscopy: The Journal of Arthroscopy and Related Surgery* (1993) 9(2):234–237.

Galili, *Immunology Today* (1993) 14(10):480–482.

Collins et al., (1994) Xenotransplantation, Characterization of Porcine Endothelial Cell Determinants Recognized by Human Natural Antibodies, 1:36–46.

Satake et al., (1994) Xenotransplantation, Limited Specificty of Xenoantibodies In Diabetic Patients Transplanted With Fetal porcine Islet Cell Clusters. Main Antibody Reactivity Against α–linked Galactose–Containing Epitopes, 1:89–101.

LaVecchio et al., (1995) Transplantation, Enzymatic Removal of Alpha–Galactosyl Epitopes From Porcine Endothelial Cells Diminished The Cytotoxic Effect of Natural Antibodies, vol. 60, 841–847.

(List continued on next page.)

*Primary Examiner*—David J. Isabella
*Attorney, Agent, or Firm*—Lappin & Kusmer LLP

[57] ABSTRACT

The invention provides an article of manufacture comprising a substantially non-immunogenic knee meniscal heterografts for implantation into humans. The invention further provides a method for preparing a knee meniscal heterograft by removing at least a portion of a meniscus from a non-human animal to provide a heterograft; washing the heterograft in saline and alcohol; subjecting the heterograft to at least one treatment selected from the group consisting of exposure to ultraviolet radiation, immersion in alcohol, ozonation, freeze/thaw cycling, and optionally to chemical crosslinking. In accordance with the invention the heterograft has substantially the same mechanical properties as the native xenogeneic meniscus.

9 Claims, 5 Drawing Sheets

OTHER PUBLICATIONS

Cotterell et al. (1995) Transplantation, The Humoral Immune Response in Human Following Cross–Perfusion of Porcine Organs, vol. 60, 861–868.

Webber et al., (1985), *Journal of Orthopedic Research*, 3, 36–42.

Rubak et al., (1982), *Acta Orthop. Scand.*, 53, 181–186.

Engkvist, Ove, (1979), *Scand. J. Plast. Reconstr. Surg.*, 13, 361–369.

Rodrigo, et al., (1978), *Clinical Orthopedics and Related Research*, 134, 342–349.

Sengupta et al., (1974), *The Journal of Bone and Joint Surgery*, 568, 167–177.

MENISCAL HETEROGRAFTS

The present invention relates to the field of treatment of injured human knee joints, and in particular, to replacement and repair of a damaged human knee joint meniscus using a substantially immunologically compatible meniscus from a non-human animal.

BACKGROUND OF THE INVENTION

The human knee is a complex joint containing spatially interrelated bones, ligaments, and cartilaginous structures which interact to create a variety of motions. Specifically, the femoral condyles articulate with the surface plateaus of the tibia, through the cartilaginous medial and lateral menisci, and all of these structures are held in place by various ligaments. By virtue of their cartilaginous nature, the medial and lateral menisci are structures comprised of cells called fibrochondrocytes, an interstitial matrix of fibers of the protein collagen, and within a ground substance formed from proteoglycans. Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

Since joint cartilage in adults does not naturally regenerate to a significant degree once it is destroyed, damaged adult menisci have historically been treated by a variety of surgical interventions including removal and replacement with prosthetic devices. An artificial knee joint having a rigid plastic femoral member and a metal tibial member is disclosed in U.S. Pat. No. 4,034,418. A number of meniscus prostheses have been devised which employ resilient materials such as silicone rubber or natural rubber, as in U.S. Pat. No. 4,344,193 and U.S. Pat. No. 4,502,161. Additional deformable, flexible resilient materials for a meniscus prosthesis such as collagen, tendon, or fibrocartilage are disclosed in U.S. Pat. No. 5,092,894 and U.S. Pat. No. 5,171,322. A cartilage replacement apparatus constructed of polyethylene plastic filled with small ball bearings or gelatinous fluid is described in U.S. Pat. No. 5,358,525. However, the known artificial prostheses have been unsatisfactory for treatment of damaged menisci, since they are deficient in the elastic, and therefore in the shock-absorbing, properties characteristic of natural menisci. Moreover, the known artificial devices have not proven able to withstand the forces inherent to routine knee joint function.

The present inventor provided improved prosthetic menisci in several of his earlier patents (U.S. Pat. No. 4,880,429; U.S. Pat. No. 5,007,934; U.S. Pat. No. 5,116,374; and U.S. Pat. No. 5,158,574). These patents generally disclose prosthetic menisci formulated from dry, porous matrices of processed natural fibers such as reconstituted cross-linked collagen, which optionally include glycosaminoglycan molecules. Generally, the source of collagen for these prosthetic menisci has been animal Achilles tendons or skin. The reconstitution process removes non-collagenous materials such as glycoproteins, proteoglycans, lipids, native glycosaminoglycans, and the like, which may confer additional elastic properties to the original tissue.

Much of the structure and many of the properties of original tissues may be retained in transplants through use of xenogeneic or heterograft materials, that is, tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel heterografts are disclosed in WO 84/03036. However, none of these disclosures describe the use of a xenograft for meniscus replacement.

Xenograft materials must be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the sidechain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immuogenic meniscal cartilage heterograft for implantation into a human in need of knee meniscus repair. The invention further provides methods for processing xenogeneic meniscal cartilage with reduced immunogenicity but with substantially native elasticity and load-bearing capabilities for heterografting into humans. The method of the invention, which may include, alone or in combination, treatment with radiation, one or more cycles of freezing and thawing, treatment with a chemical cross-linking agent, treatment with alcohol, or ozonation, provides a heterograft having substantially the same mechanical properties of a native knee meniscus.

In one embodiment, the invention provides an article of manufacture comprising a substantially non-immunogenic knee meniscal heterograft for implantation into a human.

In another embodiment, the invention provides a method of preparing a meniscal heterograft for implantation into a human, which comprises removing at least a portion of a medial or lateral meniscus from a knee joint of a non-human animal to provide a heterograft; washing the heterograft in water and alcohol; and subjecting the heterograft to at least one treatment selected from the group consisting of exposure to ultraviolet radiation, immersion in alcohol, ozonation, and freeze/thaw cycling, whereby the heterograft has substantially the same mechanical properties as the meniscus.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

The xenogeneic meniscal heterograft produced in accordance with the method of the invention is substantially non-immunogenic, while generally maintaining the mechanical properties of a native meniscus. While the meniscus may undergo some shrinkage during processing, a xenogeneic medial meniscus heterograft prepared in accordance with the invention will have the general appearance of a native medial meniscus, and a xenogeneic lateral meniscus heterograft of the invention will have the general appearance of a native lateral meniscus. The xenogeneic meniscal heterograft may also be cut into segments, each of which may be implanted into the knee of a recipient as set forth below.

The invention provides, in one embodiment, a method for preparing or processing a xenogeneic medial or lateral meniscus for engraftment into humans. As defined herein, "xenogeneic" means any non-human animal. Thus knee menisci may be harvested from any non-human animal to prepare the heterografts of the invention. Menisci from transgenic non-human animals or from genetically altered non-human animals may also be used as heterografts in accordance with the present invention. Preferably, bovine, ovine, or porcine knee joints serve as sources of the medial and lateral menisci used to prepare the heterografts. More preferably, immature pig, calf or lamb knee joints are the sources of the menisci, since the cartilage of younger animals may be inherently more elastic and engraftable than hat of older animals. Most preferably, the age of the source animal is between six and eighteen months at time of slaughter.

In the first step of the method of the invention, an intact medial or lateral meniscus is removed from the knee of a non-human animal. The joint which serves as the source of the menisci should be collected from freshly killed animals and preferably immediately placed in a suitable sterile isotonic or other tissue preserving solution. Harvesting of the joints should occur as soon as possible after slaughter of the animal and should be performed in the cold, i.e., in the approximate range 5°–20° C., to minimize enzymatic and/or bacterial degradation of the meniscal tissue. The menisci are harvested from the joints in the cold, under strict sterile technique. The joint is opened by first transecting the patellar tendon. The horns of the menisci are dissected free of adhering tissue. A small amount of bone representing a substantially cylindrical plug of approximately five millimeters in diameter by five millimeters in depth may be left attached to the horns. The meniscal synovial junction is carefully identified and freed from the meniscus tissue itself, thereby forming the heterograft.

The heterograft is then washed in about ten volumes of sterile cold water to remove residual blood proteins and water soluble materials. The heterograft is then immersed in alcohol at room temperature for about five minutes, to sterilize the tissue and to remove non-collagenous materials. A heterograft appears as a shiny "C"-shaped fibrous tissue, having generally a crescent-shaped principal surface on the top side (the "superior surface") and a generally crescent-shaped principal surface on the bottom side (the "inferior surface"), where the outer portions of the superior and inferior surfaces are joined by way of an outer lateral surface and the inner portions of the superior and inferior surfaces are joined by way of an inner lateral surface.

After alcohol immersion, the heterograft may be subjected to at least one of the treatments set forth below. When more than one treatment is applied to the heterograft, the treatments may occur in any order. In one embodiment of the method of the invention, the heterograft may be treated by exposure to radiation, for example, by being placed in an ultraviolet radiation sterilizer such as the Stragene™ Model 2400, for about fifteen minutes. In another embodiment, the heterograft may be treated by again being placed in an alcohol solution. Any alcohol solution may be used to perform this treatment. Preferably, the heterograft is placed in a 70% solution of isopropanol at room temperature. In another embodiment, the heterograft may be subjected to ozonation.

In another embodiment, the heterograft may be treated by freeze/thaw cycling. For example, the heterograft may be frozen using any method of freezing, so long as the heterograft is completely frozen, i.e., no interior warm spots remain which contain unfrozen tissue. Preferably, the heterograft is dipped into liquid nitrogen for about five minutes to perform this step of the method. More preferably, the heterograft is frozen slowly by placing it in a freezer. In the next step of the freeze/thaw cycling treatment, the heterograft is thawed by immersion in an isotonic saline bath at room temperature (about 25° C.) for about ten minutes. No external heat or radiation source is used, in order to minimize fiber degradation.

The heterograft may optionally be exposed to a chemical agent to tan or crosslink the proteins within the interstitial matrix, to further diminish or reduce the immunogenic determinants present in the heterograft. Any tanning or crosslinking agent may be used for this treatment, and more than one crosslinking step may be performed or more than one crosslinking agent may be used in order to ensure complete crosslinking and thus optimally reduce the immunogenicity of the heterograft. For example, aldehydes such as glutaraldehyde, formaldehyde, adipic dialdehyde, and the like, may be used to crosslink the collagen within the interstitial matrix of the heterograft in accordance with the method of the invention. Other suitable crosslinking agents include aliphatic and aromatic diamines, carbodiimides, diisocyanates, and the like. When glutaraldelhyde is used as the crosslinking agent, for example, the heterograft may be placed in a buffered solution containing about 0.05 to about 5.0% glutaraldehyde and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from three to five days. The crosslinking reaction should continue until the immunogenic determinants are substantially removed from the xenogeneic tissue, but the reaction should be terminated prior to significant alterations of the mechanical properties of the heterograft. When diamines are also used as crosslinking agents, the glutaraldehyde crosslinking should occur after the diamine crosslinking, so that any unreacted diamines are capped. After the crosslinking reactions have proceeded to completion as described above, the heterograft should be rinsed to remove residual chemicals, and 0.01–0.05M glycine may be added to cap any unreacted aldehyde groups which remain.

Prior to treatment, the outer lateral surface of the heterograft may optionally be pierced to increase permeability to agents used to render the heterograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the heterograft. Piercing may also be performed with a laser. In one form of the invention, one or more straight lines of punctures about three millimeters apart are established circumferentially in the outer lateral surface of the heterograft.

Prior to implantation, meniscal heterograft of the invention may be treated with limited digestion by proteolytic enzymes such as ficin or trypsin to increase tissue flexibility, or with glycosidases to remove surface carbohydrate moieties, or coated with anticalcification agents, antithrombotic coatings, antibiotics, growth factors, or other drugs which may enhance the incorporation of the heterograft into the recipient knee joint. The meniscal heterograft of the invention may be further sterilized using known methods, for example, with additional glutaraldehyde or formaldehyde treatment, ethylene oxide sterilization, propylene oxide sterilization, or the like. The heterograft may be stored frozen until required for use.

The meniscal heterograft of the invention, or a segment thereof, may be implanted into damaged human knee joints by those of skill in the art using known arthroscopic surgical techniques. Specific instruments for performing arthroscopic techniques are known to those of skill in the art, which ensure accurate and reproducible placement of meniscal implants. For meniscal cartilage replacement to succeed, the following goals are preferably accomplished:

1. The torn fragmented pieces of native meniscal cartilage must be removed.
2. The attachment sites for the meniscal horns must be anatomically placed.
3. The periphery of the meniscal implant must be attached securely enough to permit axial and rotational loads.
4. The surrounding capsule and ligaments of the knee joint must be neither excessively violated nor constrained by the fixation technique. The method of meniscal implantation described in detail below is derived from K. R. Stone, et al., *Arthroscopy: The Journal of Arthroscopic and Related Surgery* 9, 234–237 (1993); other methods of meniscal implantation may also be employed to use the xenogeneic meniscal heterografts of the present invention.

Figure 1:
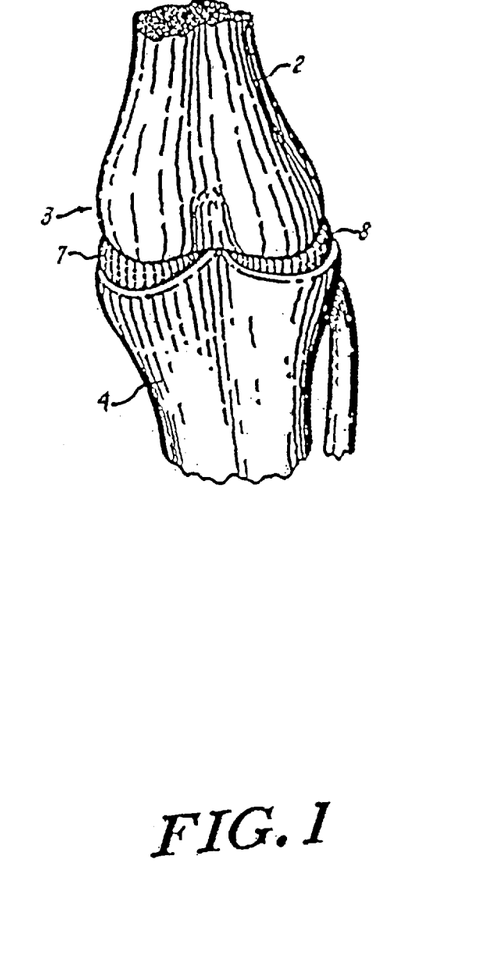
FIG. 1 shows a simplified diagrammatic representation of a human knee joint, with medial and lateral menisci in their native positions.
Figure 2:
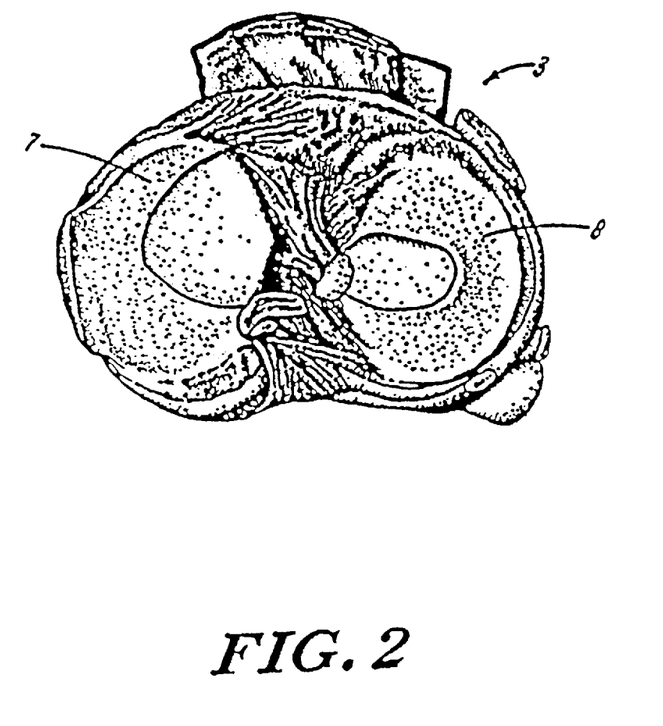
FIG. 2 is a diagrammatic representation of a cut-away view of a human knee joint, showing the medial and lateral menisci as they are positioned in vivo over the medial and lateral condyles of the tibia.
Figure 3:
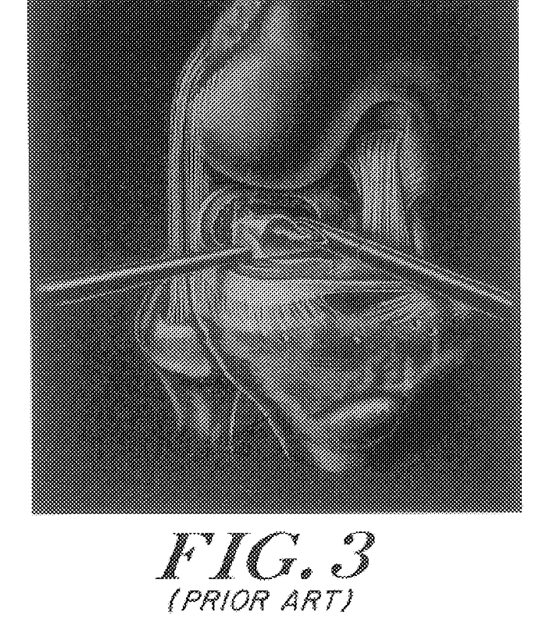
FIG. 3 is a diagrammatic representation of resection of a torn lateral meniscus of a human knee, and preparation of the knee for receipt of a meniscal implant.

Initially, complete diagnostic arthroscopy of the knee joint is accomplished using known methods. If anterior cruciate ligament surgery is to be performed simultaneously, the femoral and tibial tunnels for the cruciate reconstruction should be drilled first. The torn portion of the meniscal cartilage is evaluated. If meniscal repair cannot be accomplished due to severity of the tear or poor quality of the tissue, then preparation of the meniscal rim is undertaken by removing the torn portions of the cartilaginous tissue (FIG. 3). When the entire human meniscus is to be replaced by a xenogeneic meniscus heterograft of the invention, nearly all of the human meniscus is removed. Additionally, for replacement of the entire human meniscus with a xenogeneic meniscus heterograft of the invention, resection of the human meniscal horns and preparation of bony tunnels to accept bone plugs may be required. When only a portion of the human meniscus is to be replaced with a segment of the xenogeneic meniscus heterograft of the invention, only the damaged portions are removed, preserving the peripheral rim and horns for attachment of the xenogeneic meniscus heterograft segment. If absolutely no human meniscal rim is present, then partial replacement of the meniscus should not be performed. If the joint is excessively tight, a joint distractor may be applied or the medial collateral ligament may be partially released.

Figure 4:
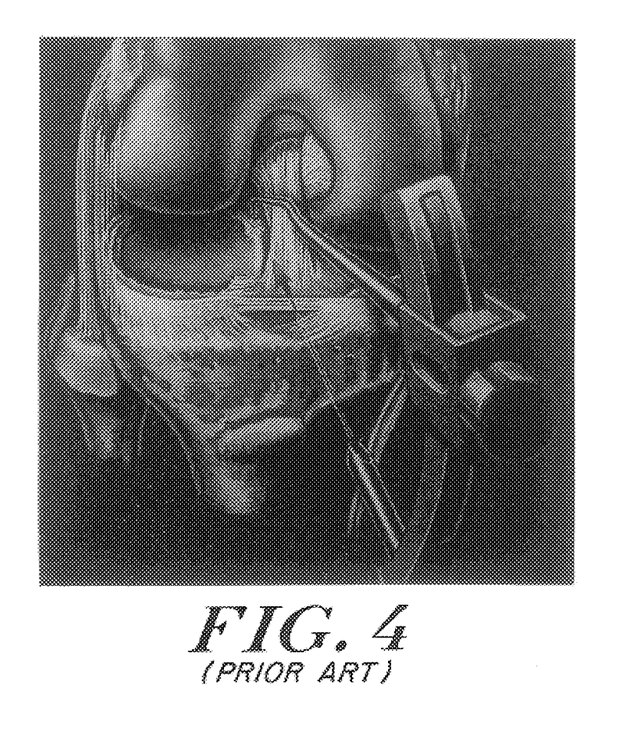
FIG. 4 is a diagrammatic representation the preferred drill guide placement for posterior lateral meniscal horn insertion into a human knee.
Figure 5:
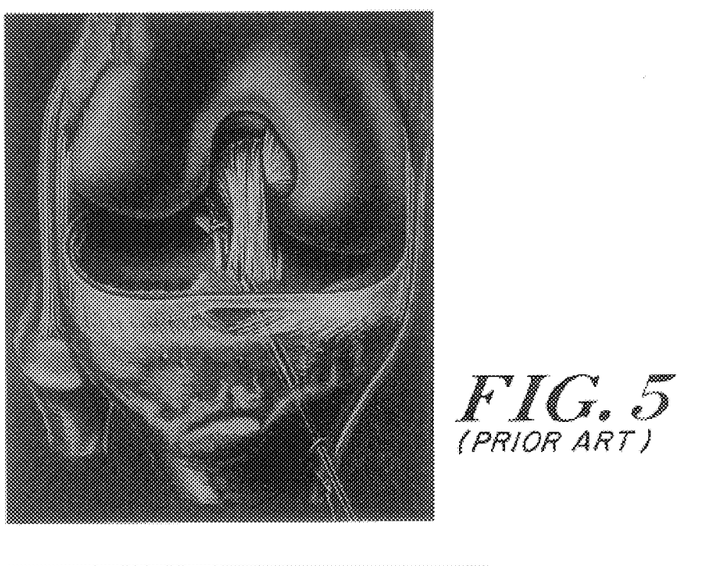
FIG. 5 is a diagrammatic representation of a cannulated drill overdrilling guide wire at the posterior lateral meniscal horn insertion into a human knee.

For medial or lateral meniscal replacement, the arthroscope is placed in the mid-lateral or anterior lateral portal and the tibial guide is placed through the anterior medial portal. The tip of the guide is brought first to the posterior horn of the meniscus. It should be noted that the posteromedial horn inserts on the posterior slope of the tibial eminence. A drill pin is then brought from the anterior medial side of the tibial tuberosity to the posterior horn insertion (FIG. 4). The pin placement can be confirmed by passing the arthroscope through the intercondylar notch and viewing the exit site of the pin. Extreme care must be undertaken to avoid penetration through the posterior capsule of the knee, endangering the neurovascular bundle. When the pin position is confirmed, the pin is then overdrilled with a 4.5-mm cannulated drill bit with the option of a drill stop to prevent posterior capsular penetration (FIG. 5). The bit is left in place and used as a tunnel for passage of a suture passer with a suture such as a #2 Ethibond™ suture available from Johnson & Johnson. The suture is passed up the bore of the drill bit, the drill bit removed, and the suture left in place.

Figure 6:
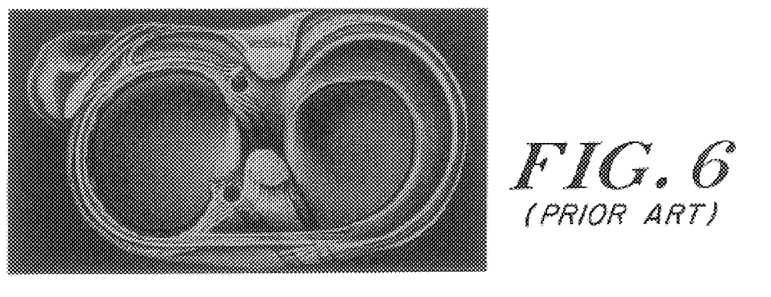
FIG. 6 is a diagrammatic representation of the appearance of a human knee with posterior and anterior drill holes for meniscal horn insertion.

The anterior medial meniscus insertion point in humans varies considerably, most often being found anterior to the medial tibial eminence. The anterior horn of the lateral meniscus inserts just posterior to the anterior cruciate ligament. An anterior drill hole is made by first identifying the insertion point of the anterior horn of the lateral meniscus, by placing the tip of the drill guide so that a relatively vertical hole will be made (FIG. 6). The drill pin is placed, then the cannulated drill bit is used to overdrill the drill pin placement to form the anterior drill hole. A suture passer is placed in the anterior drill hole. Alternatively, the anterior horn of the medial meniscus is affixed with a suture anchor directly to bone as opposed to a drill hole.

Before the suture is grasped from the anterior and posterior drill holes, the anterior portal is widened to approximately 2 cm. The suture grasper is then passed through the widened portal, and both the anterior and the posterior sutures brought out simultaneously. This technique prevents the sutures from becoming entangled in two different planes of the fat pad and capsular tissue.

Figure 7:
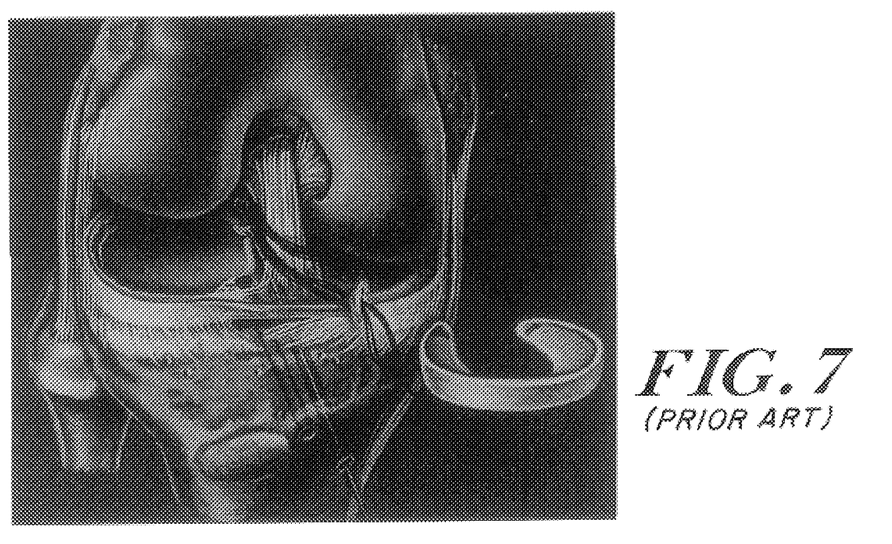
FIG. 7 is a diagrammatic representation of the preferred suture passer placement for pulling a meniscal implant into a human knee joint.
Figure 8:
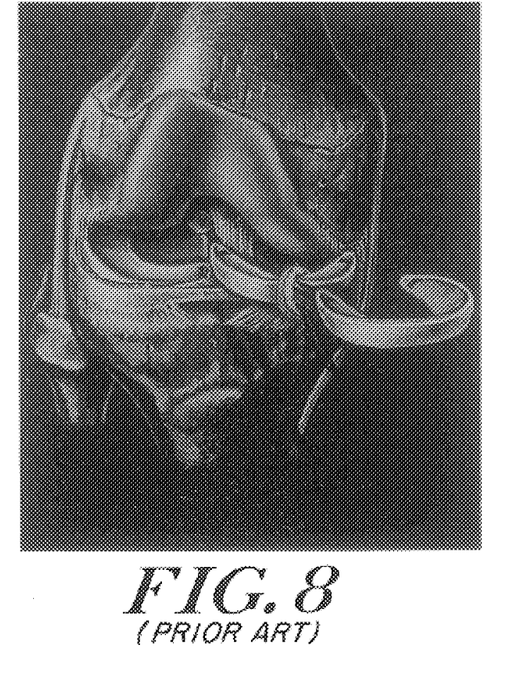
FIG. 8 is a diagrammatic representation of the appearance of a human knee containing a meniscal implant during the insertion stage.

The implant is now brought onto the field. Two horizontal mattress sutures, for example, #2-0 Ethibond™ sutures or the like, are placed through each horn of the xenogeneic meniscus heterograft with the free ends exiting the inferior surface (FIG. 7). The two posterior sutures are then drawn through the knee and out the posterior tibial tunnel (FIG. 8). If viewing from a mid-lateral portal, the anterolateral portal can be used for probe insertion to push the implant medially into place through a 1-inch incision. No insertion cannula is required. The anterior sutures are then similarly passed. The horn sutures are then tied over the anterior tibial bony bridge.

Figure 9:
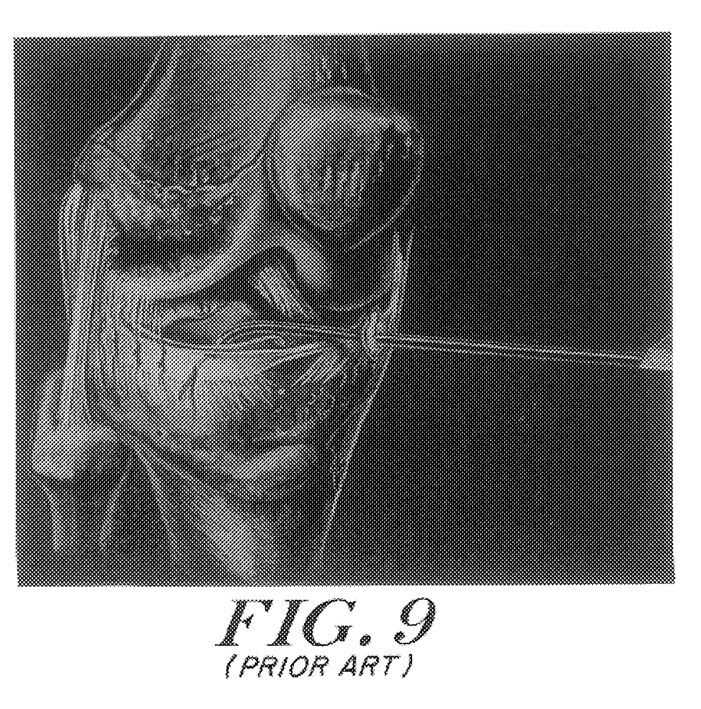
FIG. 9 is a diagrammatic representation of the appearance of a human knee containing a meniscal implant with zone-specific meniscal repair sutures in place for final tying of the meniscal repair sutures.

Next, zone specific meniscal repair cannulae are brought into place. For medial insertions, a posterior medial vertical incision is made one third of the distance from the back of the knee for protection of the saphenous nerve and for retrieval of the inside-out meniscal repair needles. A second vertical incision is usually required further anteriorly, next to the anterior medial arthroscopy portal, to capture the anterior exiting needles. Through these two incisions, the suture needles can be captured and the knots placed directly over the capsule (FIG. 9).

When using the meniscal repair needles, the posterior cannulae should be used first, with the sutures placed vertically and evenly spaced. The repair should proceed from posterior to anterior so that a buckle is not produced within the heterograft. Each knot is tied as it is placed to avoid the chance of suture tangling. The knots are spaced approximately 4 mm apart. The knee is cycled through several complete ranges of motion of ensure that the heterograft moves smoothly without impingement.

When performing a lateral meniscal replacement, the medial portal is suitable for heterograft insertion. This may require excision of the ligamentous mucosa and removal of a portion of the fat pad. The drill guide for the posterior horn of the lateral meniscus is inserted through the anteromedial portal. The posterior slope of the lateral tibial spine must be identified for accurate meniscal horn insertion. The anterior horn inserts on the anterior slope of the lateral tibial spine in approximation to the lateral aspect of the anterior cruciate ligament. The advantage of drilling these holes from the medial side is that the tunnel divergence will be greater, providing a larger bony bridge between the horn insertions. The remainder of the insertion technique remains the same, except that great care should be taken to protect the neurovascular bundle when suturing the posterior horn. Accessing posterolateral exposure is necessary to safeguard the common peroneal nerve and to expose the lateral capsule. If there is any doubt about the suture placement, open posterior horn suturing should be performed in the standard fashion.

Routine skin closure and dressings are applied. Thirty milliliters of 0.5% Marcaine (Astra) with epinephrine may be instilled if desired. A postoperative hinged knee brace is applied with the range of motion limited to 30° of extension and 90° of flexion.

Postoperatively the patient is permitted touchdown weight bearing in a hinged knee brace for six weeks. The brace is removed for sleeping and out-of-brace range-of-motion exercises. On day one after surgery, exercises are initiated for quad strengthening, including leg raises, quad sets, and well-leg bicycling. After six weeks, knee-bend exercises, two-leg bicycling, and water running exercises are initiated. When maximal strength gains are achieved, pivoting sports can be resumed, usually at four to six months after surgery.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing a meniscal heterograft for implantation into a human, which comprises
    a. removing at least a portion of a medial or lateral meniscus from a knee joint of a non-human animal to provide a heterograft;
    b. washing the heterograft in water and alcohol;
    c. subjecting the heterograft to at least one treatment selected from the group consisting of exposure to ultraviolet radiation, immersion in alcohol, ozonation, and freeze/thaw cycling, whereby the heterograft has substantially the same mechanical properties as the meniscus; and
    d. treating the hetero graft with a glycosidase to remove surface carbohydrate moieties.

2. The method according to claim 1, wherein the heterograft comprises a superior principal surface and an inferior principal surface, the outer portions of said principal surfaces being joined by an outer lateral surface, and the inner portions of said principal surfaces being joined by an inner lateral surface.

3. The method according to claim 2, comprising the further step performed prior step c of piercing the heterograft on the outer lateral surface.

4. The method according to claim 1 comprising the further step following step c of treating the heterograft with a second enzyme.

5. The method of claim 4 wherein said second enzyme is selected from the group consisting of ficin and trypsin.

6. The method of claim 1, comprising the further step following step c of treating the heterograft with one or more agents selected from the group consisting of anticalcification agents, antithrombotic agents, antibiotics, and growth factors.

7. The method of claim 1, comprising the further step following step c of sterilizing the heterograft.

8. The method of claim 7, wherein said sterilizing step is selected from the group consisting of treatment with glutaraldehyde, treatment with formaldehyde, treatment with ethylene oxide, and treatment with propylene oxide.

9. The method of claim 1, wherein the subjecting step comprises subjecting the heterograft to a treatment of freeze/thaw cycling.

* * * * *